United States Patent [19]

Kissinger et al.

[11] Patent Number: 5,362,900
[45] Date of Patent: Nov. 8, 1994

[54] PROCESS AND COMPOSITION

[75] Inventors: Gaylord M. Kissinger, Evansville, Ind.; Nicholas P. Wynn, Toronto, Canada

[73] Assignees: General Electric Co., New York, N.Y.; Sulzer Canada, Inc., Canada

[21] Appl. No.: 108,347

[22] Filed: Aug. 18, 1993

Related U.S. Application Data

[60] Division of Ser. No. 681,278, Apr. 8, 1991, Pat. No. 5,243,093, which is a continuation-in-part of Ser. No. 578,385, Sep. 7, 1990, abandoned.

[51] Int. Cl.⁵ .............................................. C07C 68/04
[52] U.S. Cl. ................................... 558/265; 558/266; 568/727
[58] Field of Search ............... 568/724, 749, 722, 727; 558/266, 265, 267

[56] References Cited

U.S. PATENT DOCUMENTS

| | | | |
|---|---|---|---|
| Re. 32,241 | 9/1986 | Saxer | 568/724 |
| 3,621,664 | 11/1971 | Saxer | 568/724 |
| 4,013,702 | 3/1977 | Cartier et al. | 558/265 |
| 4,113,974 | 9/1978 | Mark | 568/724 |
| 4,217,298 | 8/1980 | Shikata et al. | 558/265 |
| 4,354,046 | 10/1982 | Ladewig et al. | 568/724 |
| 4,927,973 | 5/1990 | Dong et al. | 568/724 |
| 5,243,093 | 4/1991 | Kissinger et al. | 568/724 |

Primary Examiner—Werren B. Lone

[57] ABSTRACT

A method comprising purifying impure bisphenol-A by fractional melt crystallization in a falling film dynamic crystallizer.

4 Claims, 1 Drawing Sheet

PROCESS AND COMPOSITION

This is a divisional of co-pending application Ser. No. 07/681,278 filed on Apr. 8, 1991, U.S. Pat. No. 5,243,093 which is a continuation-in-part of application Ser. No. 07/578,385 filed on Sep. 7, 1990 now abandoned.

BACKGROUND OF THE INVENTION

Bisphenol-A has been an extremely useful chemical for many decades. As a difunctional monomer it has been used in the preparation of numerous polymers. For example bisphenol-A (2,2-bishydroxyphenyl-propane) has been utilized in preparing inter alia, epoxy resins, polyetherimides, polyarylates and, in particular, polycarbonates. In certain of these polymer systems, particularly the epoxy systems, the purity of the bisphenol-A employed in the polymer reaction need not be that high. Epoxy resins only need bisphenol-A of approximately 95% purity. The impurity which is present in the greatest amount in such systems is generally orthopara bisphenol-A. However with other polymer systems, particularly polycarbonate, the purity of the bisphenol-A must be substantially higher. Purities of bisphenol-A of about 99.50% or higher preferably 99.80 or 99.90% or higher are desirable and in many cases necessary for the preparation of bisphenol-A polycarbonate. Therefore there has been substantial attention directed to the preparation and purification of bisphenol-A.

The art is replete with references directed to the preparation of bisphenol-A. Usually this is done by the condensation of phenol with acetone in the presence of a catalyst system. Generally the catalyst is an acidic catalyst. For many years one of the particularly useful catalyst systems in the patent art and employed commercially was hydrochloric acid. Although the economics of the process are initially good with respect to conversion of the reactants to bisphenol-A, the maintenance of the apparatus is costly. The hydrochloric acid is extremely corrosive and ordinary metallic reactors and piping must be changed on a frequent basis. Obviously glass lined reactors or certain alloyed metals can be employed, however these are quite expensive. In later years there seems to be the tendency to use a heterogeneous acidic catalyst system wherein the acidic catalyzation occurs at the catalyst surface and is actually bound to the catalyst. In this manner the "acid" does not flow with the unused reactants and bisphenol-A. Such catalyst systems are generally sulfonated polystyrenes which are substantially crosslinked such as the Amberlites and like materials. After the bisphenol-A is prepared, various isolation and purification procedures are known. Many of these appear in the relatively voluminous patent art. Generally phenol is distilled off to a great extent and/or the initial purification done by adduct crystallization of the bisphenol-A phenol adduct. Distillation of the bisphenol-A itself can also be employed. The purification of the bisphenol-A can then be accomplished through the addition of various organic solvents such as toluene or methylene chloride so as to remove the bisphenol-A from various impurities. Additionally water and various glycols such as ethylene glycol and glycerin have been used alone or together to purify the bisphenol-A from its impurities.

As stated previously the preparation of high purity bisphenol-A is extremely important in the preparation of polycarbonate. For handling purposes, storage purposes and general purity reasons, the bisphenol-A has been isolated in the orthorhombic crystal or needle (dendritic) forms, orthorhombic preferred. Until the present time, the methods of obtaining an orthorhombic crystalline form have required the use of additional water or glycols. Examples of such glycols are ethylene glycol, glycerine, butanediol and water cosolvent systems such as in U.S. Pat. No. 4,113,974. Utilization of other solvents to obtain crystalline bisphenol-A such as toluene or methylene chloride have resulted in the obtaining of the needle (dendritic) form. Each of these processes utilize such additional chemicals as organic solvents and/or water and require the utilization of such procedures as extraction, slurry handling, centrifugation, filtration, vacuum systems, distillations, dryers and waste water treatment facilities.

A new method for purifiying bisphenol-A has been discovered. None of the procedures mentioned in the last sentence of the previous paragraph need be used. This process is capable of obtaining extremely high purity bisphenol-A in a highly economic, efficient manner. The new method involves purifying impure bisphenol-A by fractional melt crystallization in a falling film dynamic crystallizer. In this manner highly pure bisphenol-A can be obtained without contamination by extraneous solvents or other materials. These results were extremely surprising since there is nothing in the art to lead one to believe that this process would work to purify bisphenol-A to such high purity levels, particularly in view of the potential contamination from degradation reactions as well as back mixing of impurities. Additionally this process is so efficient that high purity bisphenol-A can be prepared in an economically practical number of stages.

Additionally this process has the surprising aspect of freezing out the bisphenol-A in its orthorhombic crystalline form. Therefore this method produces orthorhombic crystalline bisphenol-A without the presence of additional solvents such as water, glycol or mixtures thereof. The process is extremely efficient and productive. Starting with crude bisphenol-A obtained from a reaction which prepares the bisphenol-A, high purity bisphenol-A in high yield can be prepared therefrom without the use of any or all of the following: organic solvents, water extraction, slurry handling, centrifugation, filters, vacuum systems, dryers or distillations.

SUMMARY OF THE INVENTION

In accordance with the invention there is a method comprising purifying impure bisphenol-A by fractional melt crystallization in a falling film dynamic crystallizer.

A further aspect of the invention is orthorhombic crystalline bisphenol-A in the absence of solvents such as glycol, water or mixtures thereof.

A still further aspect of the invention is the preparation of orthorhombic crystalline bisphenol-A by the fractional melt crystallization of crude bisphenol-A in a falling film dynamic crystallizer.

Additionally a still further aspect of the invention is a method of preparing pure bisphenol-A in the absence of water or organic solvents during the step of forming orthorhombic crystalline BPA.

In all of these situations orthorhombic crystalline bisphenol-A purity of at least about 99.50%, preferably at least 99.80% or 99.90% can be obtained.

DETAILED DESCRIPTION OF THE INVENTION

Figure 1:
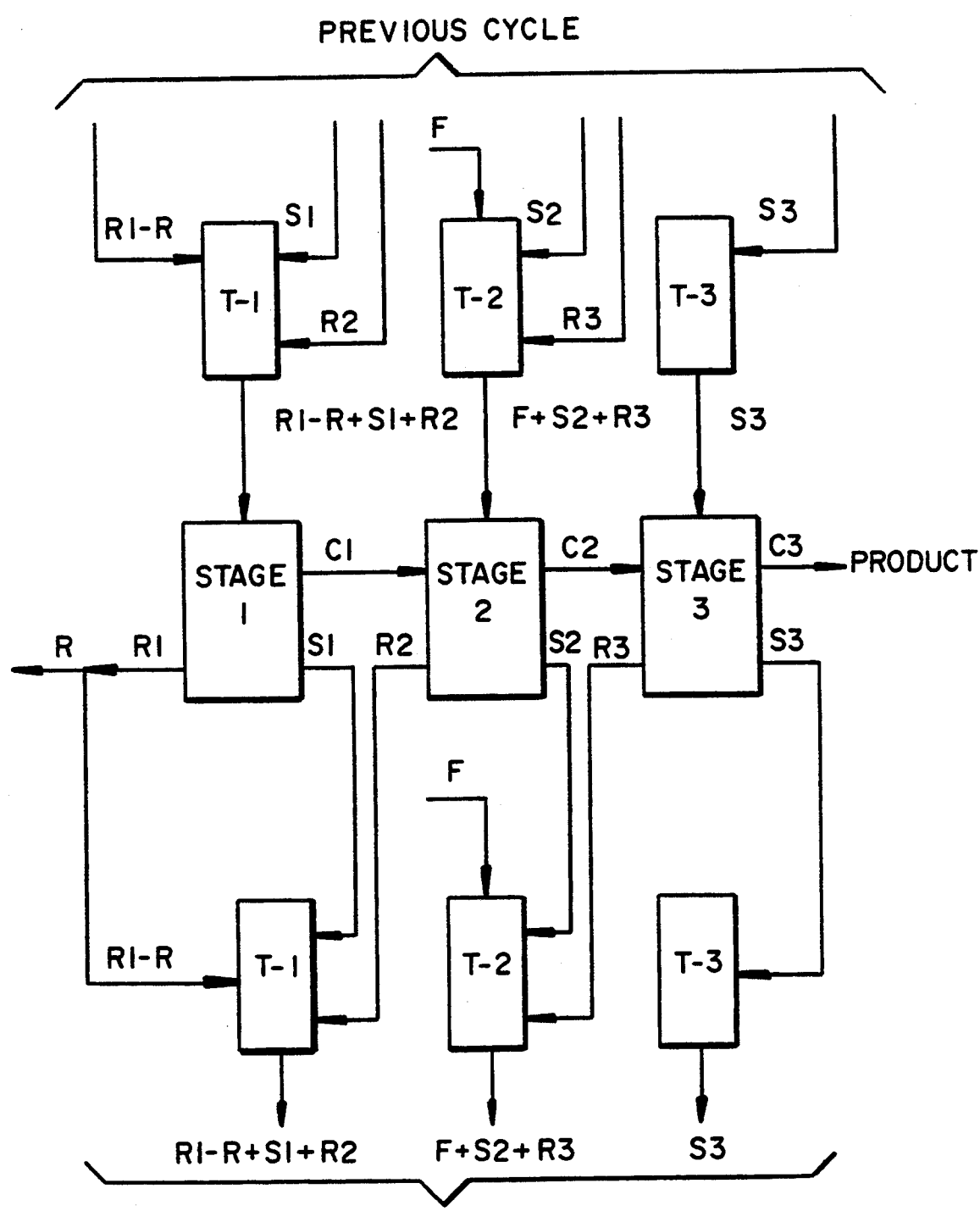

Crude bisphenol-A can be prepared by any of the art known methods. Generally this is done by an acid catalyzed condensation of phenol and acetone. The acid can be in the homogeneous state such as hydrochloric acid or it can be in an hetergeneous medium with respect to the reactants, specifically an ion exchange resin such as sulfonated crosslinked polystyrene. The bisphenol- A, unreacted reactants and side products are then removed. Usually there is substantial unreacted phenol since phenol is used in anywhere from about a 5 to 20 times molar excess. When present in such a heavy excess, substantial quantities of phenol should be removed. Frequently this is done by distillation. It is preferred to have no more than about 10 weight percent of the crude bisphenol-A solution being phenol. Preferably less than about 7% of the crude bisphenol-A composition is phenol. Also present in this crude bisphenol-A composition are side reaction products such as orthopara bisphenol-A, chroman, BPXs, dimers, spirobiindane and isopropenylphenol. Usually the unreacted acetone and water of reaction have been removed prior to or during the removal of the higher boiling excess phenol. The composition in its melt form is now subjected to fractional melt crystallization, usually multistage. The temperature is lowered gradually until the temperature is somewhat below the melting point of the desired substance, in this case bisphenol-A, MP156.7C. In some cases the composition may have to be heated above the melting temperature of the desired substance and then brought down below the freezing point. Clearly this particular procedure is advantageous in separating the desired component of a composition from impurities. Ideally, the desired component crystallizes onto the surface of the vessel holding the melt composition. The theory of the fractional melt crystallization is that the desired component preferentially is crystallized out from the melt while the undesired impurities remain in their liquid state or are entrapped in the crystalline medium to a limited extent. In a multiple stage fractional melt crystallization, the crystalline desired component's purity is upgraded in each successive stage, through the phases of crystallization, partial melting (sweating), and total melting. A preferred apparatus to carry out the fractional melt crystallization is referred to as the "Sulzer" melt crystallization apparatus. This is a falling film dynamic crystallizer, which is obtained from Sulzer Canada, Inc., a subsidiary of Sulzer Brothers, Ltd., Switzerland. An example of such an apparatus obtained from Sulzer Canada and general multistage fractional melt crystallization procedure is disclosed in detail in U.S. Pat. No. 3,621,664 issued to K. Saxer. This type of crystallizer is substantially different from a single stage, static state crystallizer, for example as shown in Konecny Czech patent publication 246681 wherein bisphenol-A is purified in a static crystallizer. The Saxer patent is incorporated by reference herein. The preferred embodiment of the invention utilizes a "Sulzer" apparatus and the continued detailed explanation of the invention is now disclosed with respect to that type of apparatus.

A crude bisphenol-A stream from which about 90% or more of the unreacted phenol as well as essentially all of the unreacted acetone and water is removed. The remaining components of the stream comprise products of the side reactions. The major component is usually o,p' bisphenol-A. The crude bisphenol-A stream is fed to a fractional melt crystallization apparatus, preferably utilizing falling films. This apparatus generally comprises a group of tubes with central distribution system to each tube, a liquid circulation system for both the heat exchange medium and the bisphenol-A containing melts, a circulation pump, a collecting tank at the bottom of the tubes, a feed tank for each stage which also functions as a holding tank for residue from crystallization phase (mother liquor) and sweat liquor, the process being conducted in multiple stages with three phases in each stage—a crystallization phase, a sweat phase and a melt phase. Each successive stage produces a purer form of the bisphenol-A, the number of stages being sufficient to obtain the desired final purity in high yield and thereby finishing one complete cycle.

The surface of the tubes is a medium on which the bisphenol-A can readily crystallize usually metal. The heat transfer medium can be inside the tube or outside, preferably on the outside of the tube. The composition which is to be crystallized is preferably inside the tube. The composition from which the desired component is to be recovered can substantially fill the tube. Similarly the heat transfer medium can substantially fill the space outside the tube. However it is preferred that both the composition to be purified and the heat transfer medium contact the inner surface and outer surface of the tube, respectively, as a film which falls from the top of the tube to the collecting reservoir. As the crude composition falls down the tube, the temperature of the heat transfer medium is lowered until the temperature of the wall on which desired compound, bisphenol-A, is crystallized is below the melting point of the bisphenol-A, for example, about 2° to 5° C. below. At this point, crystals of bisphenol-A will crystallize out on the surface of the tube. These crystals are orthorhombic in nature as shown by visualization through an aperture in the crystallization chamber. There was no predicting in advance the nature of the crystallization state. As stated previously, the only time such orthorhombic crystals had been observed was through a purification system utilizing an organic solvent such as a glycol, additional water or a mixture of water and an aprotic organic solvent as in U.S. Pat. No. 4,113,974. As the crystals build on the surface of the tube, the temperature should be gradually lowered to compensate for the thickness of the crystalline surface, and the declining freezing point of the melt. This completes the crystallization phase. The liquid which is not crystallized (residue) collects in the sump tank. At that point it can be shifted to an intermediate holding tank.

At this point the "sweat" phase can begin. In this phase of the stage, the temperature of the heat transfer medium is gradually raised. This allows some of the crystallized bisphenol-A on the tube surface to remelt, thus carrying away some of the entrapped impurities as well as adsorbed mother liquor. The sweat "liquor" is collected in the sump tank and is then passed to an intermediate holding tank for the sweat liquor. Finally, the temperature is raised significantly and the remaining crystalline bisphenol-A is melted. This completes one stage of a multi stage cycle. The purified melted bisphenol-A is now combined with the sweat liquor from a higher stage of a previous purification cycle and falls down the inside portion of the tube as a film. This feed stock is now subjected to the same three phases of crystallization, sweating and melting. The melt residue from the crystallization phase going to its holding tank, the sweat liquor to its holding tank, and the melt of crystals being of sufficient purity to be isolated in whatever form, for example prilling or flaking. The sweat liquor and crystallization residue from a previous cycle are combined and caused to fall in a film down a tube wherein the three phases of crystallization, sweating and melting are once more carried out. In this case, the residue from the crystallization phase is passed back to the bisphenol-A process as recycle. The crystal melt is combined with new crude bisphenol-A fed from the bisphenol-A process and also combined with the sweat liquor from a previous cycle and the impure residue from the previous cycle and processed in the tubes through the three phases of crystallization, sweat and melt to obtain more purified bisphenol-A, sweat liquor, and impure residue, the sweat liquor and impure residue being stored in holding tanks for the proper stage of a future cycle. This is a process wherein the three phases of crystallization, sweat and melt make up a single stage; depending upon the purity of the feed, multiple stages are generally used to obtain the purification desired and these multiple stages make up a single product cycle.

The process may also be readily understood by reference to FIG. 1 where in diagramatic form the multistage melt fractionation is illustrated. Referring to the figure, a three stage separation process comprising a product cycle is shown. These cycles are repeated continuously.

In the diagram employed, certain abbreviations are used. These abbreviations and their meanings are the following:

F = feed of crude bisphenol-A obtained from reaction preparing bisphenol-A.
$R^1$ = residue of crystallization phase not attached to tube wall from stage 1.
$R^2$ = residue of crystallization phase not attached to tube wall from stage 2.
$R^3$ = residue of crystallization phase not attached to tube wall from stage 3.
$S^1$ = liquor obtained from sweating phase in stage 1.
$S^2$ = liquor obtained from sweating phase in stage 2.
$S^3$ = liquor obtained from sweating phase in stage 3.
T-1 = holding tank for feed of stage 1.
T-2 = holding tank for feed of stage 2.
T-3 = holding tank for feed of stage 3.
$C_1$ = melted crystals phase from stage 1.
$C_2$ = melted crystals phase from stage 2.
$C_3$ = melted crystals phase from stage 3. (Product)
R = residue from stage 1, which is recycled to bisphenol-A reactor.

Referring to the diagram $R^1$—R, $S^1$ and $R^2$ are combined in the holding tank T1 and are fed into stage 1 tubes, wherein the three phases of crystallization, sweating and melting are carried out. The residue from the crystallization phase $R^1$ is taken off and a portion R is recycled to the bisphenol-A reactor. The remainder of $R^1$ is sent to the holding tank T1 for preparation of feed for another cycle. The sweating phase is now performed and the sweat liquor $S^1$ is sent to the holding tank T1. The melting phase is now performed and the bisphenol-A melt $C^1$, is brought to stage 2 as part of the feed stock for the three phases performed in stage 2. The remainder of the feed as found in holding tank T2 is $S^2$, the sweat liquor from previous cycle stage 2, $R^3$ the residue from previous crystallization phase of stage 3 and additional crude feed stock from the bisphenol-A reaction. The $C^1$ is combined with the F, $S^2$ and $R^3$ in stage 2 wherein the three phases of crystallization, sweating and melting are once more carried out. $R^2$ is sent to the holding tank T1 where it will be used as feed stock in stage 1 of the next cycle. $S^2$, the sweat liquor from stage 2 is sent to the holding tank T2 where it will be used in the feed stock of stage 2 of the next cycle. $C^2$, the bisphenol-A melt is now forwarded to stage 3 where it is combined with the $S^3$ sweat liquor produced from the previous cycle stage 3 and fed together with $C^2$ as the feed stock into stage 3. In stage 3 the three phases of crystallization, sweating and melting are carried out. $R^3$ the residue from the crystallization phase is sent to holding tank T2 wherein it will be used as feed stock for stage 2 of the following cycle. $S^3$ the sweat liquor is sent to holding tank T3 wherein it will be used as feed stock for the third stage of the following cycle. $C^3$ the melted bisphenol-A product is now of sufficient desired purity in this embodiment to be brought out from the crystallizer and isolated in any desired form, for example flake or prilled form. This bisphenol-A can now be used in the preparation of polycarbonate by standard reaction techniques such as interfacial polymerization with phosgene or melt transesterification. It should be noted that each of the tubes of the crystallizer perform each of the phases. Essentially the crystallizer tubes are in parallel, that is, the feed stock for each stage is brought up to a feeding area for all or as many of the tubes in the crystallizer as is necessary to handle the quantity of feed stock for each of the three phases of each stage. The feed stock falls in a film down the interior side of the tube as the heat exchange medium falls as a thin film on the outside of the tube.

As stated previously, when applying this process to bisphenol-A, almost all of the standard purification techniques such as phenol-bisphenol-A adduct crystallization, bisphenol-A distillation followed by purification techniques such as crystallization by solvent or water addition can be avoided. The reaction effluent can have water and acetone removed or essentially removed, most of the phenol removed—about 90 wt.% or more—and this stream fed directly to a fractional multistage melt crystallizer, preferably of the falling film type wherein the crude bisphenol-A is upgraded to a purity of better than about 99.50%, preferably better than 99.80% or 99.90%.

The figure of 90 wt.% phenol removal is not a critical number for phenol in the feed. The process will perform as well with less than 90 wt.% phenol removal, however, more stages will be needed to perform the purification of the bisphenol-A. It is preferred to have at least about 93 wt.% of the phenol removed, more preferably 97 wt.% phenol removed. The greater the phenol removal, the less residue is recycled to the reaction process for preparing bisphenol-A. Depending upon the purity of the crude bisphenol-A, as many stages as needed are performed to upgrade the purity. For example, if one desires to first go through a phenol-bisphenol-A adduct crystallization step, the bisphenol-A obtained from the adduct may need only one stage in the fractional melt crystallization falling film dynamic crystallizer to obtain the desired purity.

Below are examples of the invention. These examples are intended to provide exemplification of the invention and not limit the invention.

EXAMPLE 1

60 lb. of an impure BPA product stream prepared by for example hydrochloric acid catalyst or acidic ion exchange resin catalyst with the compositions and ultraviolet absorbance (IA and FA), as outlined in Tables 1, 2 and 3 below along with the melted crystal fraction from stage-1, and the residue and sweat liquor from stage-3, was fed to a falling film crystallizer consisting of 3 vertical tubes, each 40 ft. high and 3 inches in diameter and a 15 gallon collecting tank. The impure feed was circulated at a rate of 3 gpm to the top to fall as a film down the heat exchange surface at a starting temperature of about 166° C. It should be noted that the temperature reference for the crystallization phase is the actual residue temperature. However in the sweat and melt phases the temperature reference is to the heat exchange medium. Orthorhombic crystals of p,p' bisphenol-A were crystallized onto the heat exchange surface as the temperature was slowly ramped downward to a minimum of about 138° C. over an 85–90 minute period. This operation caused the unfrozen liquid portion of the feed to diminish in quantity to 15 lb., and increase in the amount of impurities contained in it. Once the above time and temperature conditions were met, the circulating action was stopped, and the impure liquid residue was separated away to a storage tank.

The heat exchange surface was then slowly heated for a period of about 30–35 minutes, from a starting temperature of about 154° C., and ending at about 166° C. to bring about the sweating of 4 lb. of material and cause the orthorhombic crystals frozen on the surfaces to be further purified. This liquid was separated and saved to be fed later to the next lower stage of purity (stage-1) along with the impure liquid residue obtained initially. The temperature was then raised immediately to about 171° C., causing the purified bisphenol-A to melt and collect in the sump of the crystallizer. This phase completed stage 2 which is referred to as the feed stage.

The crystal melt collected in the sump tank at the conclusion of stage-2 is now mixed with the sweat liquor from stage-4 and the crystallization residue from stage-4, altogether becoming feed to stage-3. The impure feed was circulated at a rate of 3 gpm to the top to fall as a film down the heat exchange surface at a starting temperature of about 171° C.

Orthorhombic crystals of p,p'-bisphenol-A were crystallized onto the surface as the temperature was slowly ramped downward to a minimum of about 154° C. over a 60–70 minute period. This operation caused the unfrozen liquor to diminish in quantity, to 9 lb. and increase in the amount of impurities contained in it. Once the above time and temperature conditions were met, the circulating action was stopped, and the impure liquid residue was separated away to a storage tank, to be fed to stage-2 in the following cycle.

The heat exchange surface was then slowly heated for a period of about 30–35 minutes, from a starting temperature of about 154° C., and ending at about 166° C. 3 lb. of sweat liquor or partial melt was collected and used as feed to stage-2 in the following cycle. The temperature was then raised immediately to about 171° C., causing the purified bisphenol-A to melt and collect in the sump of the crystallizer. This phase completed stage-3.

The purified melt, with no sweat liquor or crystallization residue added to it, is now circulated once again at a rate of 3 gpm to the top to fall as a film down the heat exchange surface at a starting temperature of about 171° C. Orthorhombic crystals of bisphenol-A were crystallized onto the surface as the temperature was slowly ramped downward to a minimum of about 157° C. over a period of about 30–40 minutes. 9 lbs. of unfrozen liquid from this phase containing the impurities was separated to use as feed to stage-3 in the following cycle. The temperature of the heat exchange surface was then heated slowly for about 30 minutes, beginning at about 157° C. and ending at about 166° C. 3 lbs of sweat liquor was separated and held as feed for stage-3 in the following cycle.

The temperature was then raised immediately to about 171° C., causing the purified bisphenol-A to melt, completing stage-4. This melt was then solidified on a cool surface and collected as highly purified bisphenol-A with an assay higher than 99.80%, and more specifically higher than 99.90% p,p'-bisphenol-A.

Having conducted stages-2, 3 and 4 as described, impurities were concentrated in the crystallization phase residues, which were passed downward in the process to the next lower stage of purity. Residue recovery was accomplished in stage-1, reducing the amount of bisphenol-A being recycled to the reaction process, and enhancing the yield of the process.

After accumulation of approximately 60 lb. in total of sweat liquor from stage-2, the crystallization phase residue from stage-2, and sweat liquor from stage-1, this material was charged altogether to the crystallizer for the beginning of stage-1. This feed mix was for the beginning of stage-1. This feed mix was circulated to the top at a rate of 3 gpm to fall as a film down the heat exchange surface at a starting temperature of about 171° C. Crystals of bisphenol-A were crystallized onto the surface as the temperature was slowly ramped downward to a minimum of about 115° C. over about a 90 minute period. This operation caused the unfrozen liquid portion to diminish in quantity to 26 lbs. and increase in the amount of impurities contained in it. This residue was separated to be recycled to the reaction process, or to be further recovered by another method.

After separating the impure residue, the heat exchange surface was heated for about 35 minutes, starting at about 135° C., and ending at about 154° C. 7 lbs. of sweat liquor was then separated to be fed again to stage-1 in the following cycle.

The temperature was then raised immediately to about 171° C., causing the recovered bisphenol-A to melt and collect in the crystallizer sump. This melt, when mixed with sweat liquor from stage-3, residue from stage-3 and crude bisphenol-A feed from the reaction process is added to the feed to stage-2, completing the entire cycle.

Below are the initial properties of the crude stream and the final properties of the melted orthorhombic crystalline bisphenol-A. The abbreviations are the following:

IA=Initial Absorbance
FA=Final Absorbance
IPP=Isopropenylphenol
O,P'=Orthopara BPA
Dimers=Linear and Cyclic Dimers
BPX-I=a trisphenol
CR-I=Chroman
Spiro=Spirobiindane
BPX-II=a different trisphenol
UNKS=unknown impurities
TF=Tar Factor
IYI=Initial Yellowness Index
P,P'BPA=bisphenol-A

TABLE 1

| | | | | | Typical Feed Composition | | | | | | | | |
|---|---|---|---|---|---|---|---|---|---|---|---|---|---|
| IA | FA | Phenol | IPP | O,P' | Dimers | BPX-I | CR-I | Spiro | BPX-II | UNKS | TF | IYI | P,P |
| — | — | 1.187 | 0.043 | 3.648 | 0.760 | 0.765 | 1.107 | 0.249 | 0.305 | 0.555 | 23.4 | — | 91 |

| | | | | | Typical Product Composition | | | | | | | | |
|---|---|---|---|---|---|---|---|---|---|---|---|---|---|
| IA | FA | Phenol | IPP | O,P' | Dimers | BPX-I | CR-I | Spiro | BPX-II | UNKS | TF | IYI | P,P |
| 0.085 | 0.090 | NDA | NDA | 0.048 | 0.014 | NDA | 0.005 | NDA | 0.003 | 0.009 | — | 1.10 | 99 |

TABLE 2

A Distilled Crude Bisphenol-A was Purified in a Manner Similar to Example 1

Typical Feed Composition

FEED:

| IA | FA | Phenol | IPP | O,P'BPA | Dimers | BPX-I | CR-I | Spiro | BPX-II | UNKS | TF | IYI | P,P |
|---|---|---|---|---|---|---|---|---|---|---|---|---|---|
| — | — | 0.118 | 0.214 | 2.318 | 0.931 | 0.132 | 1.245 | 0.258 | 0.227 | 0.791 | 17.0 | — | 93 |

Typcial Product Composition/Quality

PRODUCT:

| IA | FA | Phenol | IPP | O,P'BPA | Dimers | BPX-I | CR-I | Spiro | BPX-II | UNKS | TF | IYI | P,P |
|---|---|---|---|---|---|---|---|---|---|---|---|---|---|
| 0.070 | 0.092 | NDA | 0.001 | 0.059 | 0.009 | NDA | 0.002 | 0.001 | NDA | 0.010 | — | 1.04 | 99 |

A Substantially Purified Bisphenol-A As Adduct Was Used as a Feedstock and Further Purified in a Manner Similar to Example 1

Typcial Feed Analysis

FEED:

| IA | FA | Phenol | IPP | O,P' | Dimers | BPX-I | CR-1 | Spiro | BPX-II | UNKS | TF | IYI | P,P'BPA |
|---|---|---|---|---|---|---|---|---|---|---|---|---|---|
| — | — | NDA | 0.008 | 0.209 | 0.017 | 0.026 | 0.007 | NDA | 0.084 | 0.026 | 1.6 | — | 99.624 |

Typical Product Analysis

PRODUCT:

| IA | FA | Phenol | IPP | O,P' | Dimers | BPX-I | CR-1 | Spiro | BPX-II | UNKS | TF | IYI | P,P'BPA |
|---|---|---|---|---|---|---|---|---|---|---|---|---|---|
| 0.078 | 0.099 | NDA | NDA | 0.047 | 0.004 | NDA | 0.022 | NDA | 0.007 | 0.003 | — | 0.85 | 99.918 |

As stated previously the process is extremely efficient and productive. Yield, based upon the quantity of bisphenol-A in the product leaving the crystallizer divided by the quantity of bisphenol-A fed to the crystallizer, is at least about 75% per pass. Yields of up to about 98% per pass or even higher can be obtained. The quantity of yield is primarily dependent upon purity of the feed, purity of the desired product, number of stages, and the amount of bisphenol-A in the recycle residue. In the previous three examples, per pass yields of 86%, 77%, and 79% are respectively obtained.

What is claimed is:

1. An improved method for preparing polycarbonate from a purified bisphenol-A stream containing bisphenol A, phenol, acetone, water and side reaction products of an acid catalyzed condensation of phenol and acetone comprising separating from the impure bisphenol-A stream the phenol, acetone, water and side reaction products to provide a purified bisphenol-A having a purity of greater than about 99.5% and preparing polycarbonate from the purified bisphenol-A wherein the improvement comprises fractionally melt crystallizing the impure bisphenol-A stream in a falling film dynamic crystallizer.

2. An improved method for preparing polycarbonate from a purified bisphenol-A stream containing bisphenol A, phenol, acetone, water, organic solvent and side reaction products of an acid catalyzed condensation of phenol and acetone comprising separating from the impure bisphenol-A stream the phenol, acetone, water, organic solvent and side reaction products to provide a purified bisphenol-A having a purity of greater than about 99.5% and preparing polycarbonate from the purified bisphenol-A wherein the improvement comprises fractionally melt crystallizing the impure bisphenol-A stream in a falling film dynamic crystallizer.

3. The method of claim 2 wherein the organic solvent is an aromatic compound or a glycol.

4. The method of claim 2 wherein the impure bisphenol-A stream entering the falling film dynamic crystallizer contains no more than about 10 weight percent of phenol.

* * * * *